United States Patent

Nebhani

(10) Patent No.: US 9,234,089 B1
(45) Date of Patent: Jan. 12, 2016

(54) PNEUMATIC TIRE WITH SILOXY NITROXIDE

(71) Applicant: The Goodyear Tire & Rubber Company, Akron, OH (US)

(72) Inventor: Leena Nebhani, Copley, OH (US)

(73) Assignee: The Goodyear Tire & Rubber Company, Akron, OH (US)

(*) Notice: Subject to any disclaimer, the term of this patent is extended or adjusted under 35 U.S.C. 154(b) by 0 days.

(21) Appl. No.: 14/573,576

(22) Filed: Dec. 17, 2014

(51) Int. Cl.
| | |
|---|---|
| *C08K 5/32* | (2006.01) |
| *C08K 5/544* | (2006.01) |
| *C08K 3/36* | (2006.01) |
| C08K 5/34 | (2006.01) |
| B60C 1/00 | (2006.01) |
| C08K 5/5415 | (2006.01) |
| C07D 211/94 | (2006.01) |

(52) U.S. Cl.
CPC .......... *C08K 5/5442* (2013.01); *C08K 3/36* (2013.01); *B60C 1/0016* (2013.04); *C07D 211/94* (2013.01); *C08K 5/32* (2013.01); *C08K 5/34* (2013.01); *C08K 5/5415* (2013.01)

(58) Field of Classification Search
None
See application file for complete search history.

(56) References Cited

U.S. PATENT DOCUMENTS

| | | | | |
|---|---|---|---|---|
| 6,084,015 | A * | 7/2000 | Chino | ............ B60C 1/00 524/189 |
| 6,194,509 | B1 | 2/2001 | Lin | |
| 7,812,096 | B2 | 10/2010 | Ashiura et al. | |
| 8,584,725 | B2 | 11/2013 | Hahn et al. | |
| 8,686,071 | B2 | 4/2014 | Hahn et al. | |
| 2009/0156728 | A1 * | 6/2009 | Ashiura | ............ C08F 255/10 524/500 |
| 2009/0292044 | A1 | 11/2009 | Kawazura et al. | |

\* cited by examiner

*Primary Examiner* — Satya Sastri
(74) *Attorney, Agent, or Firm* — John D. DeLong

(57) ABSTRACT

The present invention is directed to a pneumatic tire comprising at least one component, the at least one component comprising a vulcanizable rubber composition, the vulcanizable rubber composition comprising: at least one diene based elastomer; precipitated silica; and a compound of formula I

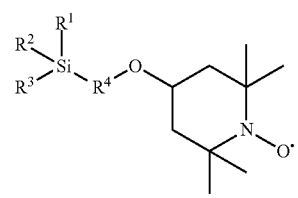

I where $R^1$, $R^2$ and $R^3$ are independently selected alkyl or alkoxy groups containing from 1 through 8 carbon atoms provided that at least one of said groups is an ethoxy group, and alternatively provided that all three of said groups are ethoxy groups, $R^4$ is an alkanediyl group containing from 0 through 8 carbon atoms, Si is silicon, N is nitrogen and O is oxygen.

18 Claims, No Drawings

PNEUMATIC TIRE WITH SILOXY NITROXIDE

BACKGROUND

Rubbery polymers are typically compounded with sulfur, accelerators, antidegradants, a filler, such as carbon black, silica or starch, and other desired rubber chemicals and are then subsequently vulcanized or cured into the form of a useful article, such as a tire or a power transmission belt. It has been established that the physical properties of such cured rubbers depend upon the degree to which the filler is homogeneously dispersed throughout the rubber. This is in turn related to the level of affinity that filler has for the particular rubbery polymer. This can be of practical importance in improving the physical characteristics of rubber articles which are made utilizing such rubber compositions. For example, the rolling resistance and traction characteristics of tires can be improved by improving the affinity of carbon black and/or silica to the rubbery polymer utilized therein. Therefore, it would be highly desirable to improve the affinity of a given rubbery polymer for fillers, such as carbon black and silica.

SUMMARY

The present invention is directed to a pneumatic tire comprising at least one component, the at least one component comprising a vulcanizable rubber composition, the vulcanizable rubber composition comprising:
  at least one diene based elastomer;
  precipitated silica; and
  a compound of formula I

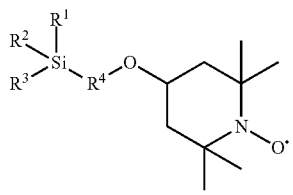

where $R^1$, $R^2$ and $R^3$ are independently selected alkyl or alkoxy groups containing from 1 through 8 carbon atoms provided that at least one of said groups is an ethoxy group, and alternatively provided that all three of said groups are ethoxy groups, $R^4$ is an alkanediyl group containing from 0 through 8 carbon atoms, Si is silicon, N is nitrogen and O is oxygen.

The invention is further directed to a method of making the tire, comprising the step of mixing at least one diene based elastomer, precipitated silica, and the compound of formula I.

DESCRIPTION

There is disclosed a pneumatic tire comprising at least one component, the at least one component comprising a vulcanizable rubber composition, the vulcanizable rubber composition comprising:
  at least one diene based elastomer;
  precipitated silica; and
  a compound of formula I

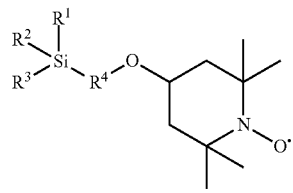

where $R^1$, $R^2$ and $R^3$ are independently selected alkyl or alkoxy groups containing from 1 through 8 carbon atoms provided that at least one of said groups is an ethoxy group, and alternatively provided that all three of said groups are ethoxy groups, $R^4$ is an alkanediyl group containing from 0 through 8 carbon atoms, Si is silicon, N is nitrogen and O is oxygen.

The present invention is directed towards the use of molecule containing nitroxide radical and siloxy functionality which can function as a modifying agent for filler surfaces as well as a coupling agent between elastomer and filler in tire formulations. The general formula I of these nitroxide radical and siloxy functionality containing molecule is shown below:

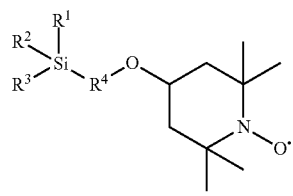

where $R^1$, $R^2$ and $R^3$ are independently selected alkyl or alkoxy groups containing from 1 through 8 carbon atoms provided that at least one of said groups is an ethoxy group, and alternatively provided that all three of said groups are ethoxy groups, $R^4$ is an alkanediyl group containing from 0 through 8 carbon atoms, Si is silicon, N is nitrogen and O is oxygen.

The molecule described in formula I above has dual functionality which provides interaction with filler as well as elastomer. As shown in the structure above, if alkoxy groups are attached to silicon they can provide interaction with hydroxyl groups on the filler surface. The functional group responsible for interaction with the elastomer is the nitroxide radical which can combine with any radicals generated on the elastomer during mixing and compounding of elastomer. Certain categories of polymers have tendency to generate more radicals, for example, natural rubber, polyisoprene. In addition, polymer containing carbon tin bond or polymer containing bonds which are thermally unstable have greater potential of generating radicals during mixing.

The rubber composition includes a compound of formula I

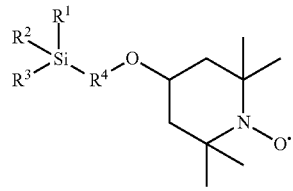

where $R^1$, $R^2$ and $R^3$ are independently selected alkyl or alkoxy groups containing from 1 through 8 carbon atoms provided that at least one of said groups is an ethoxy group, and alternatively provided that all three of said groups are ethoxy groups, $R^4$ is an alkanediyl group containing from 0 through 8 carbon atoms, Si is silicon, N is nitrogen and O is oxygen.

In one embodiment, the rubber composition includes from 0.1 to 20 phr of the compound of formula I. In one embodiment, the rubber composition includes from 0.5 to 10 phr of the compound of formula I. In one embodiment, the rubber composition includes from 1 to 5 phr of the compound of formula I.

In one embodiment, in formula I $R^4$ contains 0 carbons (a covalent bond), and $R^1$, $R^2$, $R^3$ are ethoxy.

The rubber composition includes at least one diene based rubber. Representative synthetic polymers are the homopolymerization products of butadiene and its homologues and derivatives, for example, methylbutadiene, dimethylbutadiene and pentadiene as well as copolymers such as those formed from butadiene or its homologues or derivatives with other unsaturated monomers. Among the latter are acetylenes, for example, vinyl acetylene; olefins, for example, isobutylene, which copolymerizes with isoprene to form butyl rubber; vinyl compounds, for example, acrylic acid, acrylonitrile (which polymerize with butadiene to form NBR), methacrylic acid and styrene, the latter compound polymerizing with butadiene to form SBR, as well as vinyl esters and various unsaturated aldehydes, ketones and ethers, e.g., acrolein, methyl isopropenyl ketone and vinylethyl ether. Specific examples of synthetic rubbers include neoprene (polychloroprene), polybutadiene (including cis-1,4-polybutadiene), polyisoprene (including cis-1,4-polyisoprene), butyl rubber, halobutyl rubber such as chlorobutyl rubber or bromobutyl rubber, styrene/isoprene/butadiene rubber, copolymers of 1,3-butadiene or isoprene with monomers such as styrene, acrylonitrile and methyl methacrylate, as well as ethylene/propylene terpolymers, also known as ethylene/propylene/diene monomer (EPDM), and in particular, ethylene/propylene/dicyclopentadiene terpolymers. Additional examples of rubbers which may be used include solution polymerized polymers (SBR, PBR, IBR and SIBR) functionalized with groups including but not limited to alkoxy-silyl groups, amine groups, and thioester and thiol groups. Also useful are tin-coupled polymers. The preferred rubber or elastomers are natural rubber, synthetic polyisoprene, polybutadiene and SBR.

In one aspect the rubber is preferably of at least two of diene based rubbers. For example, a combination of two or more rubbers is preferred such as cis 1,4-polyisoprene rubber (natural or synthetic, although natural is preferred), 3,4-polyisoprene rubber, styrene/isoprene/butadiene rubber, emulsion and solution polymerization derived styrene/butadiene rubbers, cis 1,4-polybutadiene rubbers and emulsion polymerization prepared butadiene/acrylonitrile copolymers.

In one aspect of this invention, an emulsion polymerization derived styrene/butadiene (E-SBR) might be used having a relatively conventional styrene content of about 20 to about 28 percent bound styrene or, for some applications, an E-SBR having a medium to relatively high bound styrene content, namely, a bound styrene content of about 30 to about 45 percent.

By emulsion polymerization prepared E-SBR, it is meant that styrene and 1,3-butadiene are copolymerized as an aqueous emulsion. Such are well known to those skilled in such art. The bound styrene content can vary, for example, from about 5 to about 50 percent. In one aspect, the E-SBR may also contain acrylonitrile to form a terpolymer rubber, as E-SBAR, in amounts, for example, of about 2 to about 30 weight percent bound acrylonitrile in the terpolymer.

Emulsion polymerization prepared styrene/butadiene/acrylonitrile copolymer rubbers containing about 2 to about 40 weight percent bound acrylonitrile in the copolymer are also contemplated as diene based rubbers for use in this invention.

The solution polymerization prepared SBR (S-SBR) typically has a bound styrene content in a range of about 5 to about 50, preferably about 9 to about 36, percent. The S-SBR can be conveniently prepared, for example, by organo lithium catalyzation in the presence of an organic hydrocarbon solvent.

In one embodiment, cis 1,4-polybutadiene rubber (BR) may be used. Such BR can be prepared, for example, by organic solution polymerization of 1,3-butadiene. The BR may be conveniently characterized, for example, by having at least a 90 percent cis 1,4-content.

The cis 1,4-polyisoprene and cis 1,4-polyisoprene natural rubber are well known to those having skill in the rubber art In one embodiment, cis 1,4-polybutadiene rubber (BR) is used. Suitable polybutadiene rubbers may be prepared, for example, by organic solution polymerization of 1,3-butadiene. The BR may be conveniently characterized, for example, by having at least a 90 percent cis 1,4-content and a glass transition temperature Tg in a range of from −95 to −105° C. Suitable polybutadiene rubbers are available commercially, such as Budene® 1207 from Goodyear and the like.

In one embodiment, a synthetic or natural polyisoprene rubber may be used.

In one embodiment, a metal coupled elastomer may be used, such as tin elastomers. Such elastomers are particularly suitable for use with the compound of formula I, as such coupled elastomers have increased potential for generating radicals during mixing.

A reference to glass transition temperature, or Tg, of an elastomer or elastomer composition, where referred to herein, represents the glass transition temperature(s) of the respective elastomer or elastomer composition in its uncured state or possibly a cured state in a case of an elastomer composition. A Tg can be suitably determined as a peak midpoint by a differential scanning calorimeter (DSC) at a temperature rate of increase of 10° C. per minute.

The term "phr" as used herein, and according to conventional practice, refers to "parts by weight of a respective material per 100 parts by weight of rubber, or elastomer."

The rubber composition may also include up to 70 phr of processing oil. Processing oil may be included in the rubber composition as extending oil typically used to extend elastomers. Processing oil may also be included in the rubber composition by addition of the oil directly during rubber compounding. The processing oil used may include both extending oil present in the elastomers, and process oil added during compounding. Suitable process oils include various oils as are known in the art, including aromatic, paraffinic, naphthenic, vegetable oils, and low PCA oils, such as MES, TDAE, SRAE and heavy naphthenic oils. Suitable low PCA oils include those having a polycyclic aromatic content of less than 3 percent by weight as determined by the IP346 method. Procedures for the IP346 method may be found in *Standard Methods for Analysis & Testing of Petroleum and Related Products* and *British Standard 2000 Parts*, 2003, 62nd edition, published by the Institute of Petroleum, United Kingdom.

The rubber composition may include from about 10 to about 150 phr of silica. The commonly employed siliceous pigments which may be used in the rubber compound include conventional pyrogenic and precipitated siliceous pigments (silica). In one embodiment, precipitated silica is used. The conventional siliceous pigments employed in this invention are precipitated silicas such as, for example, those obtained by the acidification of a soluble silicate, e.g., sodium silicate.

Such conventional silicas might be characterized, for example, by having a BET surface area, as measured using nitrogen gas. In one embodiment, the BET surface area may be in the range of about 40 to about 600 square meters per gram. In another embodiment, the BET surface area may be in a range of about 80 to about 300 square meters per gram. The BET method of measuring surface area is described in the *Journal of the American Chemical Society*, Volume 60, Page 309 (1938).

The conventional silica might be expected to have an average ultimate particle size, for example, in the range of 0.01 to 0.05 micron as determined by the electron microscope, although the silica particles may be even smaller, or possibly larger, in size.

Various commercially available silicas may be used, such as, only for example herein, and without limitation, silicas commercially available from PPG Industries under the Hi-Sil trademark with designations 210, 243, etc; silicas available from Rhodia, with, for example, designations of Z1165MP and Z165GR and silicas available from Degussa AG with, for example, designations VN2 and VN3, etc.

Commonly employed carbon blacks can be used as a conventional filler in an amount ranging from 10 to 100 phr. Representative examples of such carbon blacks include N110, N121, N134, N220, N231, N234, N242, N293, N299, N315, N326, N330, N332, N339, N343, N347, N351, N358, N375, N539, N550, N582, N630, N642, N650, N683, N754, N762, N765, N774, N787, N907, N908, N990 and N991. These carbon blacks have iodine absorptions ranging from 9 to 145 g/kg and DBP number ranging from 34 to 150 cm³/100 g.

Other fillers may be used in the rubber composition including, but not limited to, particulate fillers including ultra high molecular weight polyethylene (UHMWPE), crosslinked particulate polymer gels including but not limited to those disclosed in U.S. Pat. Nos. 6,242,534; 6,207,757; 6,133,364; 6,372,857; 5,395,891; or 6,127,488, and plasticized starch composite filler including but not limited to that disclosed in U.S. Pat. No. 5,672,639. Such other fillers may be used in an amount ranging from 1 to 30 phr.

In one embodiment the rubber composition may contain a conventional sulfur containing organosilicon compound. Examples of suitable sulfur containing organosilicon compounds are of the formula:

in which Z is selected from the group consisting of

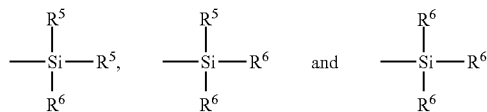

where $R^5$ is an alkyl group of 1 to 4 carbon atoms, cyclohexyl or phenyl; $R^6$ is alkoxy of 1 to 8 carbon atoms, or cycloalkoxy of 5 to 8 carbon atoms; Alk is a divalent hydrocarbon of 1 to 18 carbon atoms and n is an integer of 2 to 8.

In one embodiment, the sulfur containing organosilicon compounds are the 3,3'-bis(trimethoxy or triethoxy silylpropyl)polysulfides. In one embodiment, the sulfur containing organosilicon compounds are 3,3'-bis(triethoxysilylpropyl) disulfide and/or 3,3'-bis(triethoxysilylpropyl)tetrasulfide. Therefore, as to formula II, Z may be

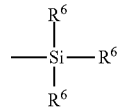

where $R^6$ is an alkoxy of 2 to 4 carbon atoms, alternatively 2 carbon atoms; alk is a divalent hydrocarbon of 2 to 4 carbon atoms, alternatively with 3 carbon atoms; and n is an integer of from 2 to 5, alternatively 2 or 4.

In another embodiment, suitable sulfur containing organosilicon compounds include compounds disclosed in U.S. Pat. No. 6,608,125. In one embodiment, the sulfur containing organosilicon compounds includes 3-(octanoylthio)-1-propyltriethoxysilane, $CH_3(CH_2)_6C(=O)—S—CH_2CH_2CH_2Si(OCH_2CH_3)_3$, which is available commercially as NXT™ from Momentive Performance Materials.

In another embodiment, suitable sulfur containing organosilicon compounds include those disclosed in U.S. Patent Publication No. 2003/0130535. In one embodiment, the sulfur containing organosilicon compound is Si-363 from Degussa.

The amount of the sulfur containing organosilicon compound in a rubber composition will vary depending on the level of other additives that are used. Generally speaking, the amount of the compound will range from 0.5 to 20 phr. In one embodiment, the amount will range from 1 to 10 phr.

It is readily understood by those having skill in the art that the rubber composition would be compounded by methods generally known in the rubber compounding art, such as mixing the various sulfur-vulcanizable constituent rubbers with various commonly used additive materials such as, for example, sulfur donors, curing aids, such as activators and retarders and processing additives, such as oils, resins including tackifying resins and plasticizers, fillers, pigments, fatty acid, zinc oxide, waxes, antioxidants and antiozonants and peptizing agents. As known to those skilled in the art, depending on the intended use of the sulfur vulcanizable and sulfur-vulcanized material (rubbers), the additives mentioned above are selected and commonly used in conventional amounts. Representative examples of sulfur donors include elemental sulfur (free sulfur), an amine disulfide, polymeric polysulfide and sulfur olefin adducts. In one embodiment, the sulfur-vulcanizing agent is elemental sulfur. The sulfur-vulcanizing agent may be used in an amount ranging from 0.5 to 8 phr, alternatively with a range of from 1.5 to 6 phr. Typical amounts of tackifier resins, if used, comprise about 0.5 to about 10 phr, usually about 1 to about 5 phr. Typical amounts of processing aids comprise about 1 to about 50 phr. Typical amounts of antioxidants comprise about 1 to about 5 phr. Representative antioxidants may be, for example, diphenyl-p-phenylenediamine and others, such as, for example, those disclosed in *The Vanderbilt Rubber Handbook* (1978), Pages 344 through 346. Typical amounts of antiozonants comprise about 1 to 5 phr. Typical amounts of fatty acids, if used, which can include stearic acid comprise about 0.5 to about 3 phr. Typical amounts of waxes comprise about 1 to about 5 phr. Often microcrystalline waxes are used. Typical amounts of peptizers comprise about 0.1 to about 1 phr. Typical peptizers may be, for example, pentachlorothiophenol and dibenzamidodiphenyl disulfide.

Accelerators are used to control the time and/or temperature required for vulcanization and to improve the properties of the vulcanizate. In one embodiment, a single accelerator system may be used, i.e., primary accelerator. The primary accelerator(s) may be used in total amounts ranging from about 0.5 to about 4, alternatively about 0.8 to about 1.5, phr. In another embodiment, combinations of a primary and a secondary accelerator might be used with the secondary accelerator being used in smaller amounts, such as from about 0.05 to about 3 phr, in order to activate and to improve the properties of the vulcanizate. Combinations of these accelerators might be expected to produce a synergistic effect on the final properties and are somewhat better than those produced by use of either accelerator alone. In addition, delayed action accelerators may be used which are not affected by normal processing temperatures but produce a satisfactory cure at ordinary vulcanization temperatures. Vulcanization retarders might also be used. Suitable types of accelerators that may be used in the present invention are amines, disulfides, guanidines, thioureas, thiazoles, thiurams, sulfenamides, dithiocarbamates and xanthates. In one embodiment, the primary accelerator is a sulfenamide. If a second accelerator is used, the secondary accelerator may be a guanidine, dithiocarbamate or thiuram compound. Suitable guanidines include dipheynylguanidine and the like. Suitable thiurams include tetramethylthiuram disulfide, tetraethylthiuram disulfide, and tetrabenzylthiuram disulfide.

The mixing of the rubber composition can be accomplished by methods known to those having skill in the rubber mixing art. For example, the ingredients are typically mixed in at least two stages, namely, at least one non-productive stage followed by a productive mix stage. The final curatives including sulfur-vulcanizing agents are typically mixed in the final stage which is conventionally called the "productive" mix stage in which the mixing typically occurs at a temperature, or ultimate temperature, lower than the mix temperature(s) than the preceding non-productive mix stage(s). The terms "non-productive" and "productive" mix stages are well known to those having skill in the rubber mixing art. The rubber composition may be subjected to a thermomechanical mixing step. The thermomechanical mixing step generally comprises a mechanical working in a mixer or extruder for a period of time suitable in order to produce a rubber temperature between 140° C. and 190° C. The appropriate duration of the thermomechanical working varies as a function of the operating conditions, and the volume and nature of the components. For example, the thermomechanical working may be from 1 to 20 minutes.

The rubber composition may be incorporated in a variety of rubber components of the tire. For example, the rubber component may be a tread (including tread cap and tread base), sidewall, apex, chafer, sidewall insert, wirecoat or innerliner. In one embodiment, the component is a tread.

The pneumatic tire of the present invention may be a race tire, passenger tire, aircraft tire, agricultural, earthmover, off-the-road, truck tire, and the like. In one embodiment, the tire is a passenger or truck tire. The tire may also be a radial or bias.

Vulcanization of the pneumatic tire of the present invention is generally carried out at conventional temperatures ranging from about 100° C. to 200° C. In one embodiment, the vulcanization is conducted at temperatures ranging from about 110° C. to 180° C. Any of the usual vulcanization processes may be used such as heating in a press or mold, heating with superheated steam or hot air. Such tires can be built, shaped, molded and cured by various methods which are known and will be readily apparent to those having skill in such art.

The invention is further illustrated by the following non-limiting examples.

EXAMPLE 1

In this example, synthesis of a siloxy nitroxide according to formula I is illustrated.

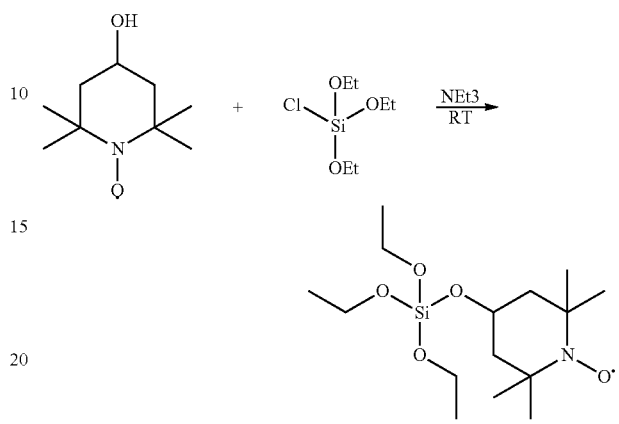

In a 100 mL round bottom flask dissolve 0.03 mol of hydroxy TEMPO (4-hydroxy-2,2,6,6-tetramethylpiperidin-1-oxyl) in 60 mL anhydrous THF. Then add 0.045 mol of triethylamine to the flask. This solution was stirred at ambient temperature for 1 hour. The flask was then placed in an ice bath and 0.024 mol of chlortriethoxysilane in 10 mL anhydrous THF was added drop wise to the flask. After addition was complete solution was stirred in an ice bath for 20 min followed by stirring at ambient temperature for 12 hours. The solid formed was filtered and solution was concentrated under reduced pressure. The material was purified using column chromatography (n-hexane:ethylacetate=9:1). The characterization was performed using 1H-NMR (for 1H-NMR equimolar quantity of phenylhydrazine was added to nitroxide molecule). 1H NMR δ (CDCl3) ppm: 1.15-1.25 (s 12H+t 9H), 1.57 (m 2H), 1.90 (m 2H), 3.85 (t 6H), 4.21 (m 1H).

EXAMPLE 2

In this example, the effect of compounding of a rubber compound with a siloxy nitroxide according to formula I is illustrated.

Siloxy nitroxide from Example 1 was mixed with polymer, silica, oil, and other compounds in a 3-piece 75 mL Brabender® mixer equipped with Banbury® rotors. Samples were mixed with additives in a mix procedure as shown in Table 1, with all amounts given in parts by weight, per 100 parts by weight of elastomer (phr). For the non-productive mix stage, compounds were mixed for 4 minutes at 60 rpm using 140° C. as starting temperature. Productive mixes were carried out using 60° C. starting temperature and 60 rpm with mix time of 3 minute.

A precipitated silica-containing rubber composition is prepared to evaluate coupling of the precipitated silica with a diene-based elastomer-containing rubber composition by an inclusion of siloxy TEMPO.

The basic rubber composition is reported in the following Table 1 with parts and percentages, where appropriate, by weight unless otherwise indicated. For example, various amounts of ingredients may be reported in terms of parts by weight per 100 parts by weight rubber (phr).

TABLE 1

| Material | Parts by weight (phr) |
|---|---|
| Non-productive mixing | |
| Styrene/butadiene rubbers[1] | 100 |
| Precipitated silica[2] | 65 |
| Silane coupling agent[3] | 5.2 |
| Compound from Example 1 | 0 and 2.0 |
| Fatty and organic acids[4] | 2.0 |
| Rubber processing oil | 11 |
| Productive mixing | |
| (subsequent to non-productive mixing) | |
| Sulfur | 1.6 |
| Sulfur cure accelerators[5] | 3.1 |
| Antioxidant[6] | 0.8 |
| Zinc oxide | 2 |

[1] Styrene/butadiene rubber, tin-coupled, 16% styrene, 42% vinyl, as SLF16S42 from Goodyear.
[2] Precipitated silica as Zeosil 1165 MP ™ from Solvay.
[3] bis (triethoxysilylpropyl) disulfide
[4] Fatty acid comprised of stearic acid, palmitic acid and oleic acid.
[5] Sulfur cure accelerators comprised of sulfenamide and diphenyl guanidine.
[6] Amine based antioxidant.

Rubber Sample A is a Control rubber Sample (SLF16S42) without siloxy TEMPO. Rubber Sample B is an experimental rubber sample (SLF16S42) which contains siloxy TEMPO.

The following Table 2 reports cure behavior and various physical properties of Control rubber Sample A and Experimental rubber Sample B upon the formulation as illustrated in Table 1 for tin coupled polymer. The rubber samples were sulfur cured, where appropriate, for about 15 minutes at about 160° C.

TABLE 2

| | A | B |
|---|---|---|
| SLF16S42 (phr) | 100 | 100 |
| Siloxy TEMPO (phr) | 0 | 2.0 |
| Cured Properties (60 minutes at 150° C.)[1] | | |
| Max torque (dNm) | 30.03 | 27.36 |
| Min torque (dNm) | 9.5 | 7.19 |
| Delta torque (dNm) | 20.53 | 20.17 |
| RPA[2] | | |
| Storage modulus (G'), 1% strain, 11 Hertz, 100° C., kPa | 2346 | 2682 |
| Storage modulus (G'), 10% strain, 11 Hertz, 100° C., kPa | 1846 | 1961 |
| Uncured Storage modulus (G'), 0.833 Hertz, 100° C., kPa | 660 | 405 |
| Tan Delta (5% strain, 100° C.) | 0.146 | 0.129 |

[1] Cure properties were determined using a Monsanto oscillating disc rheometer (MDR) which was operated at a temperature of 150° C. and at a frequency of 11 hertz. A description of oscillating disc rheometers can be found in The Vanderbilt Rubber Handbook edited by Robert O. Ohm (Norwalk, Conn., R. T. Vanderbilt Company, Inc., 1990), Pages 554 through 557. The use of this cure meter and standardized values read from the curve are specified in ASTM D-2084. A typical cure curve obtained on an oscillating disc rheometer is shown on Page 555 of the 1990 edition of The Vanderbilt Rubber Handbook.
[2] Viscoelastic properties were determined using a Flexsys Rubber Process Analyzer (RPA) 2000. A description of the RPA 2000, its capability, sample preparation, tests and subtests can be found in these references. H A Pawlowski and J S Dick, Rubber World, June 1992; J S Dick and H A Pawlowski, Rubber World, January 1997; and J S Dick and J A Pawlowski, Rubber & Plastics News, Apr. 26 and May 10, 1993.

[1] Cure properties were determined using a Monsanto oscillating disc rheometer (MDR) which was operated at a temperature of 150° C. and at a frequency of 11 hertz. A description of oscillating disc rheometers can be found in The Vanderbilt Rubber Handbook edited by Robert O. Ohm (Norwalk, Conn., R. T. Vanderbilt Company, Inc., 1990), Pages 554 through 557. The use of this cure meter and standardized values read from the curve are specified in ASTM D-2084. A typical cure curve obtained on an oscillating disc rheometer is shown on Page 555 of the 1990 edition of The Vanderbilt Rubber Handbook.

[2] Viscoelastic properties were determined using a Flexsys Rubber Process Analyzer (RPA) 2000. A description of the RPA 2000, its capability, sample preparation, tests and subtests can be found in these references. H A Pawlowski and J S Dick, Rubber World, June 1992; J S Dick and H A Pawlowski, Rubber World, January 1997; and J S Dick and J A Pawlowski, Rubber & Plastics News, Apr. 26 and May 10, 1993.

From Table 2 it is observed that the experimental rubber which contains siloxy TEMPO Sample B shows lower tan delta value (0.129) than the tan delta value (0.146) of the Control rubber Sample A which does not contains siloxy TEMPO. In addition, the uncured experimental rubber sample B exhibited better processing of with an uncured storage modulus G' of 405 kPa as compared to a higher uncured storage modulus G' of 660 kPa for the uncured rubber composition of control rubber Sample A.

Lower tan delta for Sn coupled polymer with siloxy TEMPO indicates that siloxy TEMPO helped in promoting interaction between hydroxyl groups (e.g. silanol groups) on the surface of the precipitated silica and polymer during mixing. In addition, lower uncured viscosity for polymer containing siloxy TEMPO indicated that radicals generated on polymer are trapped by siloxy TEMPO.

In addition, when the siloxy TEMPO based molecule is used in combination with functionalized polymers, it can help improve processability of functionalized polymers while maintaining desirable level of tan delta.

While certain representative embodiments and details have been shown for the purpose of illustrating the invention, it will be apparent to those skilled in this art that various changes and modifications may be made therein without departing from the spirit or scope of the invention.

What is claimed is:

1. A pneumatic tire comprising at least one component, the at least one component comprising a vulcanizable rubber composition, the vulcanizable rubber composition comprising:
   at least one diene based elastomer;
   precipitated silica; and
   a compound of formula I

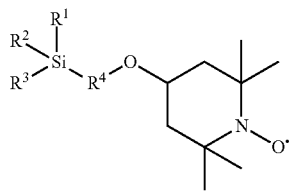

I where $R^1$, $R^2$ and $R^3$ are independently selected alkyl or alkoxy groups containing from 1 through 8 carbon atoms provided that at least one of said groups is an ethoxy group, and alternatively provided that all three of said groups are ethoxy groups, $R^4$ is an alkanediyl group containing from 0 through 8 carbon atoms, Si is silicon, N is nitrogen and O is oxygen.

2. The pneumatic tire of claim 1, wherein in formula I, $R^4$ contains 0 carbons, and $R^1$, $R^2$, $R^3$ are ethoxy.

3. The pneumatic tire of claim 1, wherein the amount of the compound of formula I ranges from 0.1 to 20 phr.

4. The pneumatic tire of claim 1, wherein the amount of the compound of formula I ranges from 0.5 to 10 phr.

5. The pneumatic tire of claim 1, wherein the amount of the compound of formula I ranges from 1 to 5 phr.

6. The pneumatic tire of claim 1, wherein the amount of silica ranges from 10 to 150 phr.

7. The pneumatic tire of claim 1, wherein the at least one diene elastomer is selected from the group consisting of are natural rubber, synthetic polyisoprene, polybutadiene and styrene-butadiene rubber.

8. The pneumatic tire of claim 1, wherein the at least one diene elastomer is a tin-coupled elastomer.

9. The pneumatic tire of claim 1, wherein the at least one diene elastomer is a functionalized elastomer.

10. A method of making a pneumatic tire, comprising the step of: mixing at least one diene based elastomer, precipitated silica, and a compound of formula I

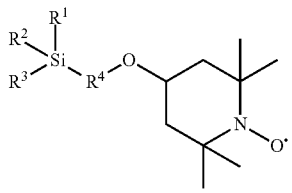

I where $R^1$, $R^2$ and $R^3$ are independently selected alkyl or alkoxy groups containing from 1 through 8 carbon atoms provided that at least one of said groups is an ethoxy group, and alternatively provided that all three of said groups are ethoxy groups, $R^4$ is an alkanediyl group containing from 0 through 8 carbon atoms, Si is silicon, N is nitrogen and O is oxygen.

11. The method of claim 10, wherein in formula I, $R^4$ contains 0 carbons, and $R^1$, $R^2$, $R^3$ are ethoxy.

12. The method of claim 10, wherein the amount of the compound of formula I ranges from 0.1 to 20 phr.

13. The method of claim 10, wherein the amount of the compound of formula I ranges from 0.5 to 10 phr.

14. The method of claim 10, wherein the amount of the compound of formula I ranges from 1 to 5 phr.

15. The method of claim 10, wherein the amount of silica ranges from 10 to 150 phr.

16. The method of claim 10, wherein the at least one diene elastomer is selected from the group consisting of are natural rubber, synthetic polyisoprene, polybutadiene and styrene-butadiene rubber.

17. The method of claim 10, wherein the at least one diene elastomer is a tin-coupled elastomer.

18. The method of claim 10, wherein the at least one diene elastomer is a functionalized elastomer.

* * * * *